United States Patent
Hoff

(10) Patent No.: US 8,846,403 B2
(45) Date of Patent: Sep. 30, 2014

(54) METHOD OF SCREENING FOR PROTEIN SECRETION RECOMBINANT HOST CELLS

(75) Inventor: Tine Hoff, Holte (DK)

(73) Assignee: Novozymes A/S, Bagsvaerd (DK)

( * ) Notice: Subject to any disclaimer, the term of this patent is extended or adjusted under 35 U.S.C. 154(b) by 1344 days.

(21) Appl. No.: 10/574,625

(22) PCT Filed: Oct. 13, 2004

(86) PCT No.: PCT/DK2004/000699
§ 371 (c)(1),
(2), (4) Date: Apr. 4, 2006

(87) PCT Pub. No.: WO2005/038024
PCT Pub. Date: Apr. 28, 2005

(65) Prior Publication Data
US 2007/0122812 A1    May 31, 2007

Related U.S. Application Data

(60) Provisional application No. 60/513,758, filed on Oct. 22, 2003.

(30) Foreign Application Priority Data

Oct. 16, 2003 (DK) .................. 2003 01526

(51) Int. Cl.
*C12N 1/20* (2006.01)
*C12N 15/75* (2006.01)
*C12N 15/10* (2006.01)

(52) U.S. Cl.
CPC ............ *C12N 15/75* (2013.01); *C12N 15/1051* (2013.01)
USPC ..................... 435/489; 435/252.31

(58) Field of Classification Search
None
See application file for complete search history.

(56) References Cited

FOREIGN PATENT DOCUMENTS

| WO | WO 96/08561 | 3/1996 |
| WO | WO 01/77315 | 10/2001 |

OTHER PUBLICATIONS

Jones et al, The Embo Journal, vol. 16, No. 21, pp. 6394-6406 (1997).
Geoffrey S. Waldo, Current Opinion, vol. 7, pp. 33-38 (2003).
Noone et al, Journal of Bacteriology, pp. 654-663 (2001).
Darmon et al, Journal of Bacteriology, pp. 5661-5671 (2002).
Speiss et al, Cell, vol. 97, pp. 339-347 (1999).
Daniels et al, XP008026411, Experimental Biology Meeting Abstracts pA584.
Noone et al, Journal of Bacteriology, pp. 1592-1599 (2000).
Dartigalongue et al, The Journal of Biological Chemistry, vol. 276, No. 24, pp. 20866-20875 (2001).
Smith et al, Journal of Bacteriology, vol. 169, No. 7, pp. 3321-3328 (1987).
Smith et al, Gene, vol. 70, pp. 351-361 (1988).
Pallen et al, Molecular Microbiology, vol. 26, No. 2, pp. 209-221 (1997).
Griffith et al, FEBS 27626, vol. 553, pp. 45-50 (2003).
Lesley et al, Protein Engineering, vol. 15, No. 2, pp. 153-160 (2002).

*Primary Examiner* — Nancy T Vogel
(74) *Attorney, Agent, or Firm* — Elias Lambiris

(57) ABSTRACT

The invention describes a method of screening for protein secreting recombinant host cells comprising screening for promoter activity of a stress inducible promoter. The method can be used for rapid identification of actively secreting transformants and can be used to screen recombinant libraries for transformants secreting proteins.

15 Claims, No Drawings

METHOD OF SCREENING FOR PROTEIN SECRETION RECOMBINANT HOST CELLS

CROSS-REFERENCE TO RELATED APPLICATIONS

This application is a 35 U.S.C. 371 national application PCT/DK2004/000699, filed Oct. 13, 2004, which claims priority or the benefit under 35 U.S.C. 119 of Danish application no. PA 2003 01526 filed Oct. 16, 2003, and U.S. provisional application No. 60/513,758 filed Oct. 22, 2003, the contents of which are fully incorporated herein by reference.

FIELD OF INVENTION

The invention describes a method of screening for protein secreting recombinant host cells. The method can be used for rapid identification of actively secreting transformants and can be used to screen recombinant libraries for transformants secreting proteins.

BACKGROUND OF THE INVENTION

Proteins which are secreted are highly interesting for use in industrial applications. A positive selection screening system which selects only host cells secreting proteins is thus very desirable.

Signal trapping is a method to identify genes containing a signal peptide using a translational fusion to an extracellular reporter gene lacking its own signal. This has been reported in the literature for the purpose of identifying new signal sequences (Smith, H. et al., 1987, Construction and use of signal sequence selection vectors in *Escherichia coli* and *Bacillus subtilis*. J. Bact. 169:3321-3328), also the use of such for defining clearly the specific elements within signal peptides which are required for optimal function (Smith, H. et al, 1988. Characterisation of signal-sequence-coding regions selected from the *Bacillus subtilis* chromosome. Gene. 70:351-361).

A further development, signal sequence trapping, has been described in WO 01/77315 (Novozymes A/S).

HtrA-type serine proteases participate in folding and degradation of aberrant proteins and in processing and maturation of native proteins (Pallen M J; Wren B W (1997): The HtrA family of serine proteases. Molecular microbiology 26: 209-221). It has been shown that the *Bacillus subtilis* YkdA and YvtA, members of this family are induced by secretion stress; when cells are expressing and secreting heterologous amylases (Noone D, Howell A, Collery R, and Kevin M. Devine (2001): YkdA and YvtA, HtrA-Like Serine Proteases in *Bacillus subtilis*, Engage in Negative Autoregulation and Reciprocal Cross-Regulation of ykdA and yvtA Gene Expression. Journal of Bacteriology 183: 654-663). This secretion stress induction happens at the transcriptional level.

SUMMARY OF THE INVENTION

The problem to be solved by the present invention is to identify those samples in a collection of host cells that efficiently secrete polypeptides, e.g. enzymes, even enzymes with unknown activity, without having to screen the collection by traditional labour- and time-consuming techniques like plasmid or genome analysis to find host cells that contain the right gene insert, thereafter to culture the selected host cells in liquid media and perform SDS-gel analysis on the host cell samples to identify the ones that are secreting recombinant protein.

We describe the introduction of one or more inducible promoters operably linked to a reporter gene into a host cell, the host cell further comprising a nucleic acid sequence of interest. The said construct may conveniently be used to screen for recombinant host cells that are secreting protein by colony colour, measuring clearing zones in substrate agars or gels, or by monitoring product formation in culturing supernatant. The invention is applicable both in expression cloning and in library screening.

Accordingly in a first aspect, the invention relates to a method of screening for protein secreting recombinant host cells comprising screening for promoter activity of a stress inducible promoter.

In a second aspect, the invention relates to a method of screening for protein secreting recombinant host cells comprising the steps of
 (i) Providing a host cell comprising the secretion stress inducible promoter operably linked to nucleic acid sequence encoding a reporter protein or a regulator protein.
 (ii) Providing a nucleic acid sequence of interest.
 (iii) Introducing the nucleic acid sequence in (ii) into the host cell in (i)
 (iv) Culturing host cell obtained in (iii) under conditions promoting expression of the protein encoded by the nucleic acid sequence from (ii); and
 (v) Selecting the host cell exhibiting the desired level of reporter protein expression.

In a particular embodiment, the regulator protein controls the expression of the reporter gene by activation or inhibition of the expression of the reporter protein.

The host cell of the present invention may be selected from bacterial cells.

In a third aspect, the invention relates to a method where the inducible promoter is comprised by or comprises the nucleic acids 1-999 of SEQ ID NO.: 1.

In a fourth aspect, the invention relates to a method where the inducible promoter is in its normal position the promoter linked to a gene encoding a polypeptide which has at least 70%, preferably 80%, or 90% or 95% or 98% identity to the amino acid sequence of SEQ ID NO.:2.

In a fifth aspect, the stress inducible promoter is comprised by or comprises the repeated octameric motif of SEQ ID NO.: 3.

In a sixth aspect, the invention relates to a method where the reporter protein is 2-fold, preferably 5-fold, or 10-fold, or 20-fold, or 50-fold or 100-fold over expressed in a secretion stressed cell compared to a non secretion stressed cell.

In a seventh aspect, the invention relates to a method where the reporter protein is selected from the group consisting of fluorescent protein, antibiotic markers, and substrate converting enzymes.

In an eighth aspect, the invention relates to a method where the host cell further comprises an IPTG-inducible promoter operably linked to a nucleic acid sequence encoding the amino acids of SEQ ID NO:2.

DEFINITIONS

Prior to a discussion of the detailed embodiments of the invention, a definition of specific terms related to the main aspects of the invention is provided.

In accordance with the present invention, there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y.: DNA Cloning: A Practical Approach, Volumes I and II/D. N. Glover ed. 1985); Oligonucleotide Synthesis (M. J. Gait ed. 1984); Nucleic Acid Hybridization (B. D. Hames & S. J. Higgins eds (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984).

Expression cloning is the optimised cloning of a gene (containing an open reading frame) into an expression vector that will allow it to be expressed at a high level in a selected host. The plasmid will in most cases contain a strong promoter region that allows a strong transcription and optimal sequences for efficient translation of the gene of interest.

Genes in a library will either be transcribed from their own promoter that might not be strong (genomic libraries), or from a promoter in the cloning vector that is typically not placed optimal for the gene to be highly expressed (genomic and cDNA libraries).

The term parent protein (e.g. "parent enzyme") may be termed wild type protein (e.g. "wild type enzyme").

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules" in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary or quaternary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA). A "recombinant DNA molecule" is a DNA molecule that has undergone a molecular biological manipulation.

A DNA "coding sequence" is a double-stranded DNA sequence, which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences.

A "gene" refers a nucleic acid sequence encoding a peptide, a polypeptide or a protein. In a particular embodiment the term "reporter gene" refers to a nucleic acid sequence encoding a reporter protein.

An "Expression vector" is a DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA, or may contain elements of both.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "secretory signal sequence" is a DNA sequence that encodes a polypeptide (a "secretory peptide" that, as a component of a larger polypeptide, directs the larger polypeptide through a secretory pathway of a cell in which it is synthesized. The larger polypeptide is commonly cleaved to remove the secretory peptide during transit through the secretory pathway.

The term "promoter" is used herein for its art-recognized meaning to denote a sequence flanking the gene containing DNA sequences that provide for the binding of RNA polymerase and initiation of transcription and furthermore it contains DNA sequences that are responsible for the regulation of the transcription of the gene. Promoter sequences are commonly, but not always, found in the 5' non-coding regions of genes. In a particular embodiment of the invention the promoter is an inducible promoter, e.g. a secretion stress induced promoter or a miss folding stress induced promoter.

"Operably linked", when referring to DNA segments, indicates that the segments are arranged so that they function in concert for their intended purposes, e.g. transcription initiates in the promoter and proceeds through the coding segment to the terminator.

A coding sequence is "under the control" of transcriptional and translational control sequences in a cell when RNA polymerase transcribes the coding sequence into mRNA, which is then trans-RNA spliced and translated into the protein encoded by the coding sequence. "Isolated polypeptide" is a polypeptide which is essentially free of other non-[enzyme] polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

"Heterologous" DNA refers to DNA not naturally located in the cell, or in a chromosomal site of the cell. Preferably, the heterologous DNA includes a gene foreign to the cell.

A cell has been "transfected" by exogenous or heterologous DNA when such DNA has been introduced inside the cell. A cell has been "transformed" by exogenous or heterologous DNA when the transfected DNA effects a phenotypic change.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A chaperone is a protein which assists another polypeptide in folding properly (Hartl et al., 1994, TIBS 19:20-25; Bergeron et al., 1994, TIBS 19:124-128; Demolder et al., 1994, Journal of Biotechnology 32:179-189; Craig, 1993, Science 260:1902-1903; Gething and Sambrook, 1992, Nature 355:

33-45; Puig and Gilbert, 1994, Journal of Biological Chemistry 269:7764-7771; Wang and Tsou, 1993, The FASEB Journal 7:1515-11157; Robinson et al., 1994, Bio/Technology 1:381-384). The nucleic acid sequence encoding a chaperone may be obtained from the genes encoding *Bacillus subtilis* GroE proteins. For further examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, Yeast 10:67-79; Fuller et al., 1989, Proceedings of the National Academy of Sciences USA 86:1434-1438; Julius et al., 1984, Cell 37:1075-1089; Julius et al., 1983, Cell 32:839-852).

The term "randomized library" of protein variants refers to a library with at least partially randomized composition of the members, e.g. protein variants.

The term "functionality" of protein variants refers to e.g. enzymatic activity, binding to a ligand or receptor, stimulation of a cellular response (e.g. 3H-thymidine incorporation as response to a mitogenic factor), or anti-microbial activity.

By the term "specific polyclonal antibodies" is meant polyclonal antibodies isolated according to their specificity for a certain antigen, e.g. the protein backbone.

"Spiked mutagenesis" is a form of site-directed mutagenesis, in which the primers used have been synthesized using mixtures of oligonucleotides at one or more positions.

DETAILED DESCRIPTION OF THE INVENTION

The present invention relates to a method of screening for protein secreting recombinant host cells comprising screening for promoter activity of a stress inducible promoter.

In a particular aspect the invention relates to a method of screening for protein secreting recombinant host cells comprising the steps of
  (i) Providing a host cell comprising the secretion stress inducible promoter operably linked to nucleic acid sequence encoding a reporter protein or a regulator protein.
  (ii) Providing a nucleic acid sequence of interest.
  (iii) Introducing the nucleic acid sequence in (ii) into the host cell in (i)
  (iv) Culturing host cell obtained in (iii) under conditions promoting secretion of the protein encoded by the nucleic acid sequence from (ii); and
  (v) Selecting the host cell exhibiting the desired level of reporter protein expression.

The host cell of the present invention may be selected from bacterial cells.
Host Cell The choice of a host cell will to a large extent depend upon the nucleic acid sequence of interest and its source. In the case where the host cell expresses an antimicrobial peptide, careful consideration should be given to the compatibility of the host cell and the expressed antimicrobial peptide.

Useful unicellular cells are bacterial cells such as gram positive bacteria including, but not limited to, a *Bacillus cell*, e.g., *Bacillus alkalophilus, Bacillus agaradhaerens, Bacillus amyloliquefaciens, Bacillus brevis, Bacillus clausii Bacillus circulans, Bacillus coagulans, Bacillus lautus, Bacillus lentus, Bacillus licheniformis, Bacillus megaterium, Bacillus stearothermophilus, Bacillus subtilis, Bacillus thuringiensis*; or a *Streptomyces* cell, e.g., *Streptomyces lividans* or *Streptomyces murinus*, or gram negative bacteria such as *E. coli* and *Pseudomonas* sp, *Pseudomonas putida*. In a preferred embodiment, the bacterial host cell is a *Bacillus lentus, Bacillus licheniformis, Bacillus stearothermophilus*, or *Bacillus subtilis* cell. In another preferred embodiment, the *Bacillus* cell is an alkalophilic *Bacillus*. Finally *Lactococcus lactis* is considered useful.

It is to be understood that any number of host cells may be included in the screening assay. In expression cloning typically 10-1000 host cells are screened, whereas library screening typically includes in the range of 500-100,000 for a Bacillus library. The host cells may also secrete different proteins as different nucleic acid sequences may have been introduced as e.g. in library screening techniques.

In another interesting embodiment, the host cell contains the inducible promoter, which is comprised by or comprises nucleic acids 1-999 of SEQ ID NO.:1 linked to a reporter gene, and further an IPTG-inducible promoter operably linked to a nucleic acid sequence encoding the amino acids of SEQ ID NO:2

The construction of the host cell (DN3) is described in Noone et al. 2000 (Noone D, Howell A, and Kevin M. Devine (2000) Expression of ykdA, Encoding a *Bacillus subtilis* Homologue of HtrA, Is Heat Shock Inducible and Negatively Autoregulated. Journal of Bacteriology 182: 1592-1599). The host contains the following features: the full ykdA promoter region (nucleic acids 1-999 of SEQ ID NO.: 1) is fused to the LacZ reporter gene. In addition an intact copy of the ykdA gene (nucleic acids 1000-2349 of SEQ ID NO.: 1) is placed under control of the IPTG-inducible Pspac promoter and the native ykdA gene is knocked out. In this way the ykdA gene itself is no longer secretion stress induced but instead ykdA expression is controllable by IPTG. The ykdA gene is negatively autoregulated. It is desirable to have a low level of the ykdA gene expressed, to avoid background expression of the reporter gene.

Inducible Promoters.

In the context of the present invention stress inducible promoter, inducible promoter and inducible promoter gene is used as synonymous. Non-limiting examples of bacillus inducible promoters are the ykdA promoter, yvtA promoter, and cssRS promoter. Two of these are members of the HtrA-like serine protease family encoded in the *B. subtilis* genome, YkdA (also called HtrA), YvtA (also called HtrB) (Hecker, M., and U. Volker. 1998. Non-specific, general and multiple stress resistance of growth-restricted *Bacillus subtilis* cells by the expression of the sigmaB regulon. Mol. Microbiol. 29:1129-1136). Promoter analysis suggests that HtrA-like proteases encoded in *B. subtilis* may have distinctive but partially overlapping expression profiles and functions within the cell. Expression of ykdA and yvtA is induced both by heat shock and by secretion stress using a common mechanism. ykdA and yvtA expression is induced in response to heterologous protein secretion or so called "secretion stress". Secretion stress inducible promoters are characterised in that they are induced by a multifactorial stimulus consisting of
  (i) the secretion load (i.e. the total number of proteins and the amount of each protein being processed and/or secreted)
  (ii) the level of protein maturation, and
  (iii) the level of aberrant protein degradation.

This multifactorial stimulus is called secretion stress, and the promoters are stress induced promoters or secretion stress induced promoters.

This has been shown by Noone et al (2001) where cells expressing and secreting recombinant amylases, showed a dramatic increase in expression of a ykda-lacZ construct in the transition phase of the growth cycle (50 fold more lacZ accumulation). A similar, but not as dramatic response was seen for a yvtA-lacZ construct. The recombinant amylase induction of both promoter-lacZ constructs occurred at the transcriptional level. Antelmann et al. (Antelmann H; Darmon E; Noone D; Veening J; Westers H; Bron S; Kuipers O P; Devine K M; Hecker M; van Dijl J M. (2003): The extracellular proteome of *Bacillus subtilis* under secretion stress conditions. Molecular Microbiology, 49: 143-156) showed by Northern blot analysis that the ykdA transcript was increased by a factor of 10-20 by heterologous amylase expression. Expression of ykdA is negatively autoregulated. This was demonstrated in cells containing the ykdA promoter linked to the beta-galactosidase reporter gene (Noone D, Howell A, and Kevin M. Devine (2000): Expression of ykdA, Encoding a *Bacillus subtilis* Homologue of HtrA, Is Heat Shock Inducible and Negatively Autoregulated. Journal of Bacteriology 182: 1592-1599). The level of beta-galactosidase steadily increases in ykdA mutant cells throughout exponential growth, in contrast to ykdA+ cells, where expression levels are low and constant. Primer extension and Northern analysis show that the regulation occurs at the level of transcription.

Members of the HtrA family of serine proteases are widely distributed among bacteria and have also been found in yeast, plants, and humans. Information derived from completely sequenced genomes shows that most eubacteria have a single HtrA-like serine protease. However, a significant number of bacterial genomes encode more than one HtrA-like serine protease. Mycobacterium tuberculosis has four such genes; *Escherichia coli, Bacillus subtilis, Treponema pallidum, Deinococcus radiodurans*, and *Synechocystis* each have three copies, while *Haemophilus influenzae* and *Pseudomonas aeruginosa* each have two copies. In some archaebacteria a recognizable member of the HtrA-protease family has also been identified.

The proteins belonging to the HtrA family are characterized by an amino-terminal domain that participates in protein localization, a catalytic domain containing an active serine residue, and a PDZ domain that functions in multimerisation of the protein into the active dodecamer structure and perhaps also in identification of target proteins. Recent work has shown that HtrA can function both as a molecular chaperone and as a protease (Spiess et al. 1999). The switch between these activities is temperature dependent, with the chaperone activity predominating at lower temperatures and the protease activity predominating at high temperature.

YkdA and yvta are regulated by the two component system CssR-CssS of the membrane. CssR-CssS responds to heat and secretion stress by activating the expression of ykdA and yvta (Darmon E; Noone D; Masson A; Bron S; Kuipers O P; Devine K M; van Diji J M (2002): A novel class of heat and secretion stress-responsive genes is controlled by the autoregulated CssRS two-component system of *Bacillus subtilis*. Journal of Bacteriology 184: 5661-5671). Misfolded proteins can accumulate in the cell through thermal denaturation or from a limited availability of appropriate folding catalysts at the extracytoplasmic side. The synthesis of proteases at elevated levels is one of a variety of cellular responses that counteract the detrimental effects of the presence of misfolded proteins. The latter mechanism would operate particularly on high-level production of secreted proteins. In this respect, it is important to bear in mind that most proteins of *B. subtilis* are transported across the membrane in an unfolded conformation via the Sec translocation channel (Tjalsma, H., A. Bolhuis, J. D. Jongbloed, S. Bron, and J. M. van Dijl. 2000: Signal peptide-dependent protein transport in *Bacillus subtilis*: a genome-based survey of the secretome. Microbiol. Mol. Biol. Rev. 64:515-547). The CssRS two-component regulatory system detects secretion stress by sensing the accumulation of misfolded proteins at the membrane-cell wall interface (Hyyryläinen, H. K., A. Bolhuis, E. Darmon, L. Muukkonen, P. Koski, M. Vitikainen, M. Sarvas, Z. Prágai, S. Bron, J. M. van Dijl, and V. P. Kontinen (2001): A novel two-component regulatory system of *Bacillus subtilis* for the survival of severe secretion stress. Mol. Microbiol. 41:1159-1172). The CssRS-inducing signal is not cytosolic misfolded proteins, since neither htrA nor htrB expression is induced by puromycin addition, which stops protein synthesis in the cell. The present observation that the expression of CssRS-controlled genes is responsive both to heat and secretion stress indicates that the CssRS system can sense misfolded proteins extracytosolically, irrespective of the cause that leads to their accumulation. The cssRS operon it self was shown to be transcriptionally induced by secretion stress caused by overproduction of a heterologous protein (Darmon et al. 2002). This was detected by an increase in reportergene activity in a host expressing a recombinant amylase and containing the cssRS operon promoter fused to the bgaB reporter.

Comparison of the three secretion stress-inducible promoters, ykdA, yvtA and cssRS show that they a 1 1 three contain repeated octameric motifs identical or close to TTTTCATA (SEQ ID NO.:3). It has been demonstrated that a point mutation in repeat I of the octameric consensus sequence affects heat and secretion stress induction of both the yvtAB and cssRS genes (Darmon et al. 2002). These data show that stress-induced expression of yvtA and cssRS are linked through this common regulatory sequence, perhaps to make the levels of protease (YkdA and yvtA) and regulator (CssR and CssS) responsive to the prevailing stress conditions. The CssRS system of *Bacillus* bears some resemblance to the CpxA-CpxR two-component system from *E. coli*. First, CpxA and CssS show amino acid sequence similarities, and the same is true for CpxR and CssR (Hyyryläinen et al. 2001). Second, these two systems control the transcription of genes encoding HtrA-like proteases: htrA (degp) of *E. coli* is regulated by the CpxAR system, and ykdA and yvtA of *B. subtilis* is regulated by the CssRS system. Finally, like the cpxAR operon, the transcription of the cssRS operon is autoregulated.

Functional homologs are defined as proteins with similar functions. As example homologs of HtrA proteases are proteins with similar functions, i.e. proteases induced by secretion stress and misfolded (aberrant) proteins.

Yet in another interesting aspect of the invention the inducible promoter in its normal position is the promoter linked to a gene encoding a polypeptide which has at least 70%, preferably 80% or 90%, more preferably at least 95% or 98% identity to the amino acid sequence of SEQ ID NO.:2. The term "normal position" is this context to be understood as the occurrence of the promoter as it is found when operably linked to a protein not protein engineered.

The degree of identity between two amino acid sequences is determined by the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters are Ktuple=1, gap penalty=3, windows=5, and diagonals=5. The degree of identity between two nucleotide sequences may be determined using the same algorithm and software package as described above with the following settings: Gap penalty of 10, and gap length penalty of 10. Pair wise alignment parameters are Ktuple=3, gap penalty=3 and windows=20.

The method of the present invention may also used to identify new stress induced promoters by providing a host cell capable of secreting a protein and introduce a possible stress inducible promoter operably linked to a nucleic acid sequence encoding a reporter protein or a regulator protein into the host cell. By selecting the host cell exhibiting the desired level of reporter protein expression host cells containing stress inducible promoters may be identified and subsequently the stress inducible promoter may be isolated by techniques used in the art.

The use of more than one inducible promoter may be advantageous for the purpose of screening.

Reporter Protein.

Reporter genes are nucleic acid sequences encoding easily assayed proteins (hereinafter reporter proteins). Reporter genes are frequently used as indicators of transcriptional activity or activation of particular signalling pathways within the cell.

In the method of the present invention, the inducible promoter gene may be operably linked to a nucleic acid sequence encoding a reporter protein which is expressed when the inducible promoter is activated as described above.

Alternatively, the expression of the reporter protein may be controlled by a regulator protein operably linked to the stress inducible promoter. A regulator protein is a protein that control the expression of a gene by interacting with a control site in DNA an influencing the initiation of transcription. The regulator gene may act as an activator, i.e. act as a positive regulator of transcription or as a repressor, i.e. decrease the level of transcription.

Measuring the amount of reporter protein expressed by the host cell obviously depends on the choice of reporter protein, but non-limiting examples are given below.

Commonly used reporter proteins are chloramphenicol acetyltransferase, beta-galactosidase, beta-glucuronidase, aequorin, Green fluorescent protein, Red fluorescent protein, Blue fluorescent protein, Yellow fluorescent protein, luciferase, lux, heme, antibiotic markers, alkaline phosphatase, and beta-lactamase Nucleic Acid Sequence.

In the method of the present invention a nucleic acid sequence of interest may be obtained in various ways known in the art. Non-limiting examples are: isolation of wild type genes, generation of protein engineered variants, site directed mutagenesis, library screening. The host cell may comprise one or more, e.g. 2-15, particularly 2-10, more particularly 2-4, chromosomally integrated copies of the nucleic acid sequence of interest. The nucleic acid sequence of interest may be cloned on a plasmid and remain on the plasmid in the cell.

As used herein the term "nucleic acid sequence" is intended to indicate any nucleic acid molecule of cDNA, genomic DNA, synthetic DNA or RNA origin. The term "sequence" is intended to indicate a nucleic acid segment which may be single- or double-stranded, and which may be based on a complete or partial nucleotide sequence encoding a polypeptide.

The nucleic acid sequence of interest may suitably be of genomic or cDNA origin, for instance obtained by preparing a genomic or cDNA library and screening for DNA sequences coding for all or part of the polypeptide by hybridization using synthetic oligonucleotide probes in accordance with standard techniques (cf. Sambrook et al., supra).

The nucleic acid sequence may also be prepared synthetically by established standard methods, e.g. the phosphoamidite method described by Beaucage and Caruthers, Tetrahedron Letters 22 (1981), 1859-1869, or the method described by Matthes et al., EMBO Journal 3 (1984), 801-805. According to the phosphoamidite method, oligonucleotides are synthesized, e.g. in an automatic DNA synthesizer, purified, annealed, ligated and cloned in suitable vectors.

Furthermore, the nucleic acid sequence may be of non cult type, mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid sequence may also be prepared by polymerase chain reaction using specific primers, for instance as described in U.S. Pat. No. 4,683,202 or Saiki et al., Science 239 (1988), 487-491.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See e.g. Innis et al., 1990, A Guide to Methods and Application, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain producing the polypeptide, or from another related organism and thus, for example, may be an allelic or species variant of the polypeptide encoding region of the nucleic acid sequence.

The term "isolated" nucleic acid sequence as used herein refers to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electorphoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

Nucleic Acid Sequence Library

Preparation of a nucleic acid sequence library can be achieved by use of known methods.

Procedures for extracting genes from a cellular nucleotide source and preparing a gene library are described in e.g. Pitcher et al., "Rapid extraction of bacterial genomic DNA with guanidium thiocyanate", Lett. Appl. Microbiol., 8, pp 151-156, 1989, Dretzen, G. et al., "A reliable method for the recovery of DNA fragments from agarose and acrylamide gels", Anal. Biochem., 112, pp 295-298, 1981, WO 94/19454 and Diderichsen et al., "Cloning of aldB, which encodes alpha-acetolactate decarboxylase, an exoenzyme from *Bacillus brevis*", J. Bacteriol., 172, pp 4315-4321, 1990.

Procedures for preparing a gene library from an in vitro made synthetic nucleotide source can be found in (e.g. described by Stemmer, Proc. Natl. Acad. Sci. USA, 91, pp. 10747-10751, 1994 or WO 95/17413).

The library can also be screened as autonomically replicating plasmid library.

Manipulating the Nucleic Acid Sequences of a Library

In a particular embodiment the genes of a gene library may before, during or after initiating the screening be subjected to alterations and or mutations by genetic engineering. Generation of libraries of genes encoding variants of enzymes can be done in a variety of ways:

(1) Error prone PCR employs a low fidelity replication step to introduce random point mutations at each round of amplification (Caldwell and Joyce (1992), PCR Methods and Applications vol. 2 (1), pp. 28-33). Error-prone PCR mutagenesis is performed using a plasmid encoding the wild-type, i.e. wt, gene of interest as template to amplify this gene with flanking primers under PCR conditions where increased error rates leads to introduction of random point mutations. The PCR conditions utilized are typically: 10 mM Tris-HCl, pH 8.3, 50 mM KCl, 4 mM $MgCl_2$, 0.3 mM $MnCl_2$, 0.1 mM dGTP/dATP, 0.5 mM dTTP/dCTP, and 2.5 u Taq polymerase per 100 micro L of reaction. The resultant PCR fragment is purified on a gel and cloned using standard molecular biology techniques.

(2) Oligonucleotide directed mutagenesis in single codon position (including deletions or insertions), e.g. by SOE-PCR is described by Kirchhoff and Desrosiers, PCR Methods and Applications, 1993, 2, 301-304. This method is performed as follows: Two independent PCR reactions are performed with 2 internal, overlapping primers, wherein one or both contain a mutant sequence and 2 external primers, which may encode restriction sites, thereby creating 2 overlapping PCR fragments. These PCR fragments are purified, diluted, and mixed in molar ratio 1:1. The full length PCR product is subsequently obtained by PCR amplification with the external primers. The PCR fragment is purified on gel and cloned using standard molecular biology techniques.

(3) Oligonucleotide directed randomization in single codon position, such as saturation mutagenesis, may be done e.g. by SOE-PCR as described above, but using primers with randomized nucleotides. For example NN(G/T), wherein N is any of the 4 bases G,A,T or C, will yield a mixture of codons encoding all possible amino acids.

(4) Combinatorial site-directed mutagenesis libraries may be employed, where several codons can be mutated at once using (2) and (3) above. For multiple sites, several overlapping PCR fragments are assembled simultaneously in a SOE-PCR setup.

(5) Another protocol employs synthetic gene libraries preparation. Wild type, i.e. wt, genes can be assembled from multiple overlapping oligonucleotides (typically 40-100 nucleotides in length; (Stemmer et al., (1995), Gene 164, 49-53). By including mixtures of wt and mutant variants of the same oligo at various positions in the gene, the resulting assembled gene will contain mutations at various positions with mutagenic rates corresponding to the ratios of wt to mutant primers.

(6) Still another method employs multiple mutagenic primers to generate libraries with multiple mutated positions. First an uracil-containing nucleotide template encoding a polypeptide of interest is generated and 2-50 mutagenic primers corresponding to at least one region of identity in the nucleotide template are synthezised so that each mutagenic primer comprises at least one substitution of the template sequence (or: insertion/deletion of bases) resulting in at least one amino acid substitution (or insertion/deletion) of the amino acid sequence encoded by the uracil-containing nucleotide template. The mutagenic primers are then contacted with the uracil-containing nucleotide template under conditions wherein a mutagenic primer anneals to the template sequence. This is followed by extension of the primer(s) catalyzed by a polymerase to generate a mixture of mutagenized polynucleotides and uracil-containing templates. Finally, a host cell is transformed with the polynucleotide and template mixture wherein the template is degraded and the mutagenized polynucleotide replicated, generating a library of polynucleotide variants of the gene of interest.

(7) Libraries may be created by shuffling e.g. by recombination of two or more wt genes or genes encoding variant proteins created by any combination of methods (1)-(6) (above) by DNA shuffling.

In the method of the present invention, the nucleic acid sequence may be introduced into the host cell in the form of a nucleic acid construct.

Nucleic Acid Constructs

The present invention also relates to nucleic acid constructs comprising a nucleic acid sequence of the present invention operably linked to one or more control sequences that direct the expression of the coding sequence in a suitable host cell under conditions compatible with the control sequences.

A nucleic acid sequence encoding a polypeptide of the present invention may be manipulated in a variety of ways to provide for expression of the polypeptide. Manipulation of the nucleotide sequence prior to its insertion into a vector may be desirable or necessary depending on the expression vector. The techniques for modifying nucleotide sequences utilizing recombinant DNA methods are well known in the art.

The control sequence may be an appropriate promoter sequence, a nucleotide sequence which is recognized by a host cell for expression of the nucleotide sequence. The promoter sequence contains transcriptional control sequences, which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

The control sequence may also be a signal peptide coding region that codes for an amino acid sequence linked to the amino terminus of a polypeptide and directs the encoded polypeptide into the cell's secretory pathway. The 5' end of the coding sequence of the nucleotde sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57:109-137.

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems.

Expression Vectors

The present invention also relates to recombinant expression vectors comprising the nucleic acid construct of the invention. The various nucleotide and control sequences described above may be joined together to produce a recombinant expression vector which may include one or more convenient restriction sites to allow for insertion or substitution of the nucleotide sequence encoding the polypeptide at such sites. Alternatively, the nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome.

The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dalgenes from *Bacillus subtilis* or *Bacillus licheniformis*, or markers which confer antibiotic resistance such as ampicillin, kanamycin, chloramphenicol or tetracycline resistance.

The vectors of the present invention preferably contain an element(s) that permits stable integration of the vector into the host cell's genome or autonomous replication of the vector in the cell independent of the genome.

For integration into the host cell genome, the vector may rely on the nucleotide sequence encoding the polypeptide or any other element of the vector for stable integration of the vector into the genome by homologous or nonhomologous recombination. Alternatively, the vector may contain additional nucleotide sequences for directing integration by homologous recombination into the genome of the host cell. The additional nucleotide sequences enable the vector to be integrated into the host cell genome at a precise location(s) in the chromosome(s). To increase the likelihood of integration at a precise location, the integrational elements should preferably contain a sufficient number of nucleotides, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleotide sequence of the present invention may be inserted into the host cell to increase production of the gene product. An increase in the copy number of the nucleotide sequence can be obtained by integrating at least one additional copy of the sequence into the host cell genome or by including an amplifiable selectable marker gene with the nucleotide sequence where cells containing amplified copies of the selectable marker gene, and thereby additional copies of the nucleotide sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Transformation

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

Enzymes.

A particular embodiment of the present invention is the secretion of enzyme, where the enzyme may be selected from the group of enzymes comprising glycosyl hydrolases, carbohydrases, peroxidases, proteases, lipases, phytases, polysaccharide lyases, oxidoreductases, transglutaminases and glycoseisomerases, in particular the following.

Parent Proteases

Parent proteases (i.e. enzymes classified under the Enzyme Classification number E.C. 3.4 in accordance with the Recommendations (1992) of the International Union of Biochemistry and Molecular Biology (IUBMB)) include proteases within this group.

Examples include proteases selected from those classified under the Enzyme Classification (E.C.) numbers:

3.4.11 (i.e. so-called aminopeptidases), including 3.4.11.5 (Prolyl aminopeptidase), 3.4.11.9 (X-pro aminopeptidase), 3.4.11.10 (Bacterial leucyl aminopeptidase), 3.4.11.12 (Thermophilic aminopeptidase), 3.4.11.15 (Lysyl aminopeptidase), 3.4.11.17 (Tryptophanyl aminopeptidase), 3.4.11.18 (Methionyl aminopeptidase).

3.4.21 (i.e. so-called serine endopeptidases), including 3.4.21.1 (Chymotrypsin), 3.4.21.4 (Trypsin), 3.4.21.25 (Cucumisin), 3.4.21.32 (Brachyurin), 3.4.21.48 (Cerevisin) and 3.4.21.62 (Subtilisin); 3.4.22 (i.e. so-called cysteine endopeptidases), including 3.4.22.2 (Papain), 3.4.22.3 (Ficain).

3.4.22.6 (Chymopapain), 3.4.22.7 (Asclepain), 3.4.22.14 (Actinidain), 3.4.22.30 (Caricain) and 3.4.22.31 (Ananain);

3.4.23 (i.e. so-called aspartic endopeptidases), including 3.4.23.1 (Pepsin A), 3.4.23.18 (Aspergillopepsin I), 3.4.23.20 (Penicillopepsin) and 3.4.23.25 (Saccharopepsin); and 3.4.24 (i.e. so-called metalloendopeptidases), including 3.4.24.28 (Bacillolysin).

Examples of relevant subtilisins comprise subtilisin BPN, subtilisin amylosacchariticus, subtilisin 168, subtilisin mesentericopeptidase, subtilisin Carlsberg, subtilisin DY, subtilisin 309, subtilisin 147, thermitase, aqualysin, *Bacillus* PB92 protease, proteinase K, Protease TW7, and Protease TW3.

Specific examples of such readily available commercial proteases include Esperase®), Alcalase®, Neutrase®, Dyrazym®, Savinase (D, Pyrase®), Pancreatic Trypsin NOVO (PTN), Bio-Feed® Pro, Clear-Lens Pro® (all enzymes available from Novozymes A/S).

Examples of other commercial proteases include Maxtase®, Maxacal®, Maxapem® marketed by Gist-Brocades N.V., Opticlean® marketed by Solvay et Cie. and Purafect® marketed by Genencor International.

It is to be understood that also protease variants are contemplated as the parent protease. Examples of such protease variants are disclosed in EP 130.756 (Genentech), EP 214.435 (Henkel), WO 87/04461 (Amgen), WO 87/05050 (Genex), EP 251.446 (Genencor), EP 260.105 (Genencor), Thomas et al., (1985), Nature. 318, p. 375-376, Thomas et al., (1987), J. Mol. Biol., 193, pp. 803-813, Russel et al., (1987), Nature, 328, p. 496-500, WO 88/08028 (Genex), WO 88/08033 (Amgen), WO 89/06279 (Novo Nordisk A/S), WO 91/00345 (Novo Nordisk A/S), EP 525 610 (Solvay) and WO 94/02618 (Gist-Brocades N.V.).

The activity of proteases can be determined as described in "Methods of Enzymatic Analysis", third edition, 1984, Verlag Chemie, Weinheim, vol. 5.

Parent Lipases

Parent lipases (i.e. enzymes classified under the Enzyme Classification number E.C. 3.1.1 (Carboxylic Ester Hydrolases) in accordance with the Recommendations (1992) of the International Union of Biochemistry and Molecular Biology (IUBMB)) include lipases within this group.

Examples include lipases selected from those classified under the Enzyme Classification (E.C.) numbers:

3.1.1 (i.e. so-called Carboxylic Ester Hydrolases), including (3.1.1.3) Triacylglycerol lipases, (3.1.1.4.) Phosphorlipase A2.

Examples of lipases include lipases derived from the following microorganisms: *Humicola*, e.g. *H. brevispora, H. lanuginosa, H. brevis* var. *thermoidea* and *H. insolens* (U.S. Pat. No. 4,810,414).

*Pseudomonas*, e.g. *Ps. fragi, Ps. stutzeri, Ps. cepacia* and *Ps. fluorescens* (WO 89/04361), or *Ps. plantarii* or *Ps. gladioli* (U.S. Pat. No. 4,950,417 (Solvay enzymes)) or *Ps. alcaligenes* and *Ps. pseudoalcaligenes* (EP 218 272) or *Ps. mendocina* (WO 88/09367; U.S. Pat. No. 5,389,536).

*Fusarium*, e.g. *F. oxysporum* (EP 130,064) or *F. solani* pisi (WO 90/09446).

*Mucor* (also called Rhizomucor), e.g. *M. miehei* (EP 238 023).

*Chromobacterium* (especially *C. viscosum*). *Aspergillus* (especially *A. niger*).

*Candida*, e.g. *C. cylindracea* (also called *C. rugosa*) or *C. antarctica* (WO 88/02775) or *C. antarctica* lipase A or B (WO 94/01541 and WO 89/02916). *Geotricum*, e.g. *G. candidum* (Schimada et al., (1989), J. Biochem., 106, 383-388). *Penicillium*, e.g. *P. camembertii* (Yamaguchi et al., (1991), Gene 103, 61-67). *Rhizopus*, e.g. *R. delemar* (Hass et al., (1991), Gene 109, 107-113) or *R. niveus* (Kugimiya et al., (1992) Biosci. Biotech. Biochem 56, 716-719) or *R. oryzae*.

*Bacillus*, e.g. *B. subtilis* (Dartois et al., (1993) Biochemica et Biophysica acta 1131, 253-260) or *B. stearothermophilus* (JP 64/7744992) or *B. pumilus* (WO 91/16422).

Specific examples of readily available commercial lipases include Lipolase®, Lipolase® Ultra, Lipozyme®, Palatase®, Novozym® 435, Lecitase) (all available from Novozymes A/S). Examples of other lipases are Lumafast®, *Ps. mendocian* lipase from Genencor Int. Inc.; Lipomax®, *Ps. pseudoalcaligenes* lipase from Gist Brocades/Genencor Int. Inc.; *Fusarium solani* lipase (cutinase) from Unilever; *Bacillus* sp. lipase from Solvay enzymes. Other lipases are available from other companies.

It is to be understood that also lipase variants are contemplated as the parent enzyme. Examples of such are described in e.g. WO 93/01285 and WO 95/22615.

The activity of the lipase can be determined as described in "Methods of Enzymatic Analysis", Third Edition, 1984, Verlag Chemie, Weinhein, vol. 4, or as described in AF 95/5 GB (available on request from Novozymes A/S).

Parent Oxidoreductases

Parent oxidoreductases (i.e. enzymes classified under the Enzyme Classification number E.C. 1 (Oxidoreductases) in accordance with the Recommendations (1992) of the International Union of Biochemistry and Molecular Biology (IUBMB)) include oxidoreductases within this group.

Examples include oxidoreductases s elected from those classified under the Enzyme Classification (E.C.) numbers: Glycerol-3-phosphate dehydrogenase _NAD+_ (1.1.1.8), Glycerol-3-phosphate dehydrogenase _NAD(P)+_ (1.1.1.94), Glycerol-3-phosphate 1-dehydrogenase _NADP_ (1.1.1.94), Glucose oxidase (1.1.3.4), Hexose oxidase (1.1.3.5), Catechol oxidase (1.1.3.14), Bilirubin oxidase (1.3.3.5), Alanine dehydrogenase (1.4.1.1), Glutamate dehydrogenase (1.4.1.2), Glutamate dehydrogenase _NAD(P)+_ (1.4.1.3), Glutamate dehydrogenase _NADP+_ (1.4.1.4), L-Amino acid dehydrogenase (1.4.1.5), Serine dehydrogenase (1.4.1.7), Valine dehydrogenase _NADP+_ (1.4.1.8), Leucine dehydrogenase (1.4.1.9), Glycine dehydrogenase (1.4.1.10), L-Amino-acid oxidase (1.4.3.2.), D-Amino-acid oxidase (1.4.3.3), L-Glutamate oxidase (1.4.3.11), Protein-lysine 6-oxidase (1.4.3.13), L-lysine oxidase (1.4.3.14), L-Aspartate oxidase (1.4.3.16), D-amino-acid dehydrogenase (1.4.99.1), Protein disulfide reductase (1.6.4.4), Thioredoxin reductase (1.6.4.5), Protein disulfide reductase (glutathione) (1.8.4.2), Laccase (1.10.3.2), Catalase (1.11.1.6), Peroxidase (1.11.1.7), Lipoxygenase (1.13.11.12), Superoxide dismutase (1.15.1.1)

Said Glucose oxidases may be derived from *Aspergillus niger*. Said Laccases may be derived from *Polyporus pinsitus, Myceliophtora thermophila, Coprinus cinereus, Rhizoctonia solani, Rhizoctonia praticola, Scytalidium thermophilum* and *Rhus vernicifera*. Bilirubin oxidases may be derived from *Myrothechecium verrucaria*. The Peroxidase may be derived from e.g. Soy bean, Horseradish or *Coprinus cinereus*. The Protein Disulfide reductases Protein Disulfide reductases of bovine origin, Protein Disulfide reductases derived from *Aspergillus oryzae* or *Aspergillus niger*, and DsbA or DsbC derived from *Escherichia coli*.

Specific examples of readily available commercial oxidoreductases include Gluzyme (enzyme available from Novozymes AIS). However, other oxidoreductases are available from others.

It is to be understood that also variants of oxidoreductases are contemplated as the parent enzyme.

The activity of oxidoreductases can be determined as described in "Methods of Enzymatic Analysis", third edition, 1984, Verlag Chemie, Weinheim, vol. 3.

Parent Carbohydrases

Parent carbohydrases may be defined as all enzymes capable of breaking down carbohydrate chains (e.g. starches) of especially five and six member ring structures (i.e. enzymes classified under the Enzyme Classification number E.C. 3.2 (glycosidases) in accordance with the Recommendations (1992) of the International Union of Biochemistry and Molecular Biology (IUBMB)).

Examples include carbohydrases selected from those classified under the Enzyme Classification (E.C.) numbers: alfa-amylase (3.2.1.1) alfa-amylase (3.2.1.2), glucan 1,4-alfa-glucosidase (3.2.1.3), cellulase (3.2.1.4), endo-1,3(4)-beta-glucanase (3.2.1.6), endo-1,4-beta-xylanase (3.2.1.8), dextranase (3.2.1.11), chitinase (3.2.1.14), polygalacturonase (3.2.1.15), lysozyme (3.2.1.17), beta-glucosidase (3.2.1.21), alfa-galactosidase (3.2.1.22), beta-galactosidase (3.2.1.23), amylo-1,6-glucosidase (3.2.1.33), xylan 1,4-beta-xylosidase (3.2.1.37), glucan endo-1,3-beta-D-glucosidase (3.2.1.39), alfa-dextrin endo-1,6-glucosidase (3.2.1.41), sucrose alfa-glucosidase (3.2.1.48), glucan endo-1,3-alfa-glucosidase (3.2.1.59), glucan 1,4-beta-glucosidase (3.2.1.74), glucan endo-1,6-beta-glucosidase (3.2.1.75), arabinan endo-1,5-alfa-arabinosidase (3.2.1.99), lactase (3.2.1.108), and chitonanase (3.2.1.132).

Specific examples of readily available commercial carbohydrases include Alpha-Gal®, Bio-Feed® Alpha, Bio-Feed® Beta, Bio-Feed® Plus, Bio-Feed® Plus, Novozyme®) 188, Carezyme®), Celluclast®), Cellusoft®), Ceremyl®, Citrozym®, Denimax®, Dezyme®, Dextrozyme®, Finizym®, Fungamyl®, Gamanase®, Glucanex®, Lactozym®, Maltogenase®, Pentopan®, Pectinex®, Promozyme®, Pulpzyme®, Novamyl®, Termamyl®, AMG (Amyloglucosidase Novo), Maltogenase®), Aquazym®, Natalase® (all enzymes available from Novozymes A/S). Other carbohydrases are available from other companies.

It is to be understood that also carbohydrase variants are contemplated as the parent enzyme.

The activity of carbohydrases can be determined as described in "Methods of Enzymatic Analysis", third edition, 1984, Verlag Chemie, Weinheim, vol. 4.

Parent Transferases

Parent transferases (i.e. enzymes classified under the Enzyme Classification number E.C. 2 in accordance with the Recommendations (1992) of the International Union of Biochemistry and Molecular Biology (IUBMB)) include transferases within this group.

The parent transferases may be any transferase in the sub-groups of transferases: transferases transferring one-carbon groups (E.C. 2.1); transferases transferring aldehyde or residues (E.C 2.2); acyltransferases (E.C. 2.3); glucosyltransferases (E.C. 2.4); transferases transferring alkyl or aryl groups, other that methyl groups (E.C. 2.5); transferases transferring nitrogeneous groups (2.6).

In a preferred embodiment the parent transferase is a transglutaminase E.C 2.3.2.13 (Protein-glutamine beta-glutamyl-transferase).

Transglutaminases are enzymes capable of catalyzing an acyl transfer reaction in which a gamma-carboxyamide group of a peptide-bound glutamine residue is the acyl donor. Primary amino groups in a variety of compounds may function as acyl acceptors with the subsequent formation of monosubstituted gamma-amides of peptide-bound glutamic acid. When the epsilon-amino group of a lysine residue in a peptide-chain serves as the acyl acceptor, the transferases form intramolecular or intermolecular gamma-glutamyl-epsilon-lysyl crosslinks.

The parent transglutaminase may be of human, animal (e.g. bovine) or microbial origin.

Examples of such parent transglutaminases are animal derived Transglutaminase, FXIIa; microbial transglutaminases derived from *Physarum polycephalum* (Klein et al., Journal of Bacteriology, Vol. 174, p. 2599-2605); transglutaminases derived from *Streptomyces* sp., including *Streptomyces lavendulae, Streptomyces lydicus* (former *Streptomyces libani*) and *Streptoverticillium* sp., including *Streptoverticillium mobaraense, Streptoverticillium cinnamoneum,* and *Streptoverticillium griseocarneum* (Motoki et al., U.S. Pat. No. 5,156,956; Andou et al., U.S. Pat. No. 5,252,469; Kaempfer et al., Journal of General Microbiology, Vol. 137, p. 1831-1892; Ochi et al., International Journal of Sytematic Bacteriology, Vol. 44, p. 285-292; Andou et al., U.S. Pat. No. 5,252,469; Williams et al., Journal of General Microbiology, Vol. 129, p. 1743-1813).

It is to be understood that also transferase variants are contemplated as the parent enzyme.

The activity of transglutaminases can be determined as described in "Methods of Enzymatic Analysis", third edition, 1984, Verlag Chemie, Weinheim, vol. 1-10.

Parent Phytases

Parent phytases are included in the group of enzymes classified under the Enzyme Classification number E.C. 3.1.3 (Phosphoric Monoester Hydrolases) in accordance with the Recommendations (1992) of the International Union of Biochemistry and Molecular Biology (IUBMB)).

Phytases are enzymes produced by microorganisms, which catalyse the conversion of phytate to inositol and inorganic phosphorus.

Phytase producing microorganisms comprise bacteria such as *Bacillus subtilis, Bacillus natto* and *Pseudomonas*; yeasts such as *Saccharomyces cerevisiae*; and fungi such as *Aspergillus niger, Aspergillus ficuum, Aspergillus awamori, Aspergillus oryzae, Aspergillus terreus* or *Aspergillus nidulans*, and various other *Aspergillus* species).

Examples of parent phytases include phytases selected from those classified under the Enzyme Classification (E.C.) numbers: 3-phytase (3.1.3.8) and 6-phytase (3.1.3.26).

The activity of phytases can be determined as described in "Methods of Enzymatic Analysis", third edition, 1984, Verlag Chemie, Weinheim, vol. 1-10, or may be measured according to the method described in EP-A1-0 420 358, Example 2 A.

Lyases Suitable lyases include Polysaccharide lyases: Pectate lyases (4.2.2.2) and pectin lyases (4.2.2.10), such as those from *Bacillus licheniformis* disclosed in WO 99/27083.

Isomerases

Without being limited thereto suitable protein disulfide isomerases (PDI) include PDls described in WO 95/01425 (Novo Nordisk A/S) and suitable glucose isomerases include those described in Biotechnology Letter, Vol. 20, No 6, June 1998, pp. 553-56.

Contemplated isomerases include xylose/glucose Isomerase (5.3.1.5) including Sweetzyme□ (available from Novozymes AIS).

Antimicrobial Peptides.

In another particular embodiment of the present invention, the secreted protein is an anti microbial peptide (AMP). In the context of the present invention AMPs are polypeptides or proteins showing evidence of antimicrobial activity.

The term "antimicrobial activity" is defined herein as an activity which is capable of killing or inhibiting growth of microbial cells. In the context of the present invention the term "antimicrobial" is intended to mean that there is a bactericidal and/or a bacteriostatic and/or fungicidal and/or fungistatic effect and/or a virucidal effect, wherein the term "bactericidal" is to be understood as capable of killing bacterial cells. The term "bacteriostatic" is to be understood as capable of inhibiting bacterial growth, i.e. inhibiting growing bacterial cells. The term "fungicidal" is to be understood as capable of killing fungal cells. The term "fungistatic" is to be understood as capable of inhibiting fungal growth, i.e. inhibiting growing fungal cells. The term "virucidal" is to be understood as capable of inactivating virus. The term "microbial cells" denotes bacterial or fungal cells (including yeasts).

In the context of the present invention the term "inhibiting growth of microbial cells" is intended to mean that the cells are in the non-growing state, i.e., that they are not able to propagate.

For purposes of the present invention, antimicrobial activity may be determined according to the procedure described by Lehrer et al., Journal of Immunological Methods, Vol. 137 (2) pp. 167-174 (1991).

Polypeptides having antimicrobial activity may be capable of reducing the number of living cells of a microbe selected from the group consisting of *Aspergillus fumigatus* (CBS 113.26), *Candida albicans* (ATCC 10231), *Saccharomyces cerevisiae* (ATCC 9763), *Trychophyton mentagrophytes* (DSM 4870), *Pityrosporum* (CBS 1878), *Epidermophyton floccosum* (DSM 10709), *Aspergillus niger* (ATCC 9642) and *Fusarium* Oxysporum to 1/100 after 30 min. incubation at 20° C. in an aqueous solution of 25%(w/w); preferably in an aqueous solution of 10%(w/w); more preferably in an aqueous solution of 5%(w/w); even more preferably in an aqueous solution of 1%(w/w); most preferably in an aqueous solution of 0.5%(w/w); and in particular in an aqueous solution of 0.1%(w/w).

Polypeptides having antimicrobial activity may also be capable of inhibiting the outgrowth of a microbe selected from the group consisting of *Aspergillus fumigatus* (CBS 113.26), *Candida albicans* (ATCC 10231), *Saccharomyces cerevisiae* (ATCC 9763), *Trychophyton mentagrophytes* (DSM 4870), *Pityrosporum* (CBS 1878), *Epidermophyton floccosum* (DSM 10709), *Aspergillus niger* (ATCC 9642) and *Fusarium Oxysporum* for 24 hours at 25° C. in a microbial growth substrate, when added in a concentration of 1000 ppm; preferably when added in a concentration of 500 ppm; more preferably when added in a concentration of 250 ppm; even more preferably when added in a concentration of 100 ppm; most preferably when added in a concentration of 50 ppm; and in particular when added in a concentration of 25 ppm.

An AMP of the present invention may be obtained from microorganisms of any genus. For purposes of the present invention, the term "obtained from" as used herein shall mean that the polypeptide encoded by the nucleotide sequence is produced by a cell in which the nucleotide sequence is naturally present or into which the nucleotide sequence has been inserted. In a preferred embodiment, the polypeptide is secreted extracellularly.

An AMP of the present invention may be a bacterial polypeptide. For example, the polypeptide may be a gram positive bacterial polypeptide such as a *Bacillus polypeptide*, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide; or a *Streptomyces* polypeptide, e.g., a *Streptomyces lividans* or *Streptomyces murinus* polypeptide; or a gram negative bacterial polypeptide, e.g., an *E. coli* or a *Pseudomonas* sp. polypeptide.

An AMP of the present invention may be a fungal polypeptide, and more preferably a yeast polypeptide such as a *Candida, Kluyveromyces, Pichia, Saccharomyces, Schizosaccharomyces*, or *Yarrowia* polypeptide; or more preferably a filamentous fungal polypeptide such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide.

In an interesting embodiment, the polypeptide is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* polypeptide.

In another interesting embodiment, the polypeptide is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammiung von Mikroorganismen und Zelikulturen GmbH (DSM), Centraalbureau Voor Schimmelcultures (CBS), and Agricultural Research Service Patent Culture Collection, Northern Regional Research Center (NRRL).

AMPs encoded by nucleotide sequences of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof encoding another polypeptide to a nucleotide sequence (or a portion thereof) of the present invention.

Methods of Production.

The transformed or transfected host cells described above are cultured in a suitable nutrient medium under conditions permitting the production of the desired molecules, after which these are recovered from the cells, or the culture broth.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The media are prepared using procedures known in the art (see, e.g., references for bacteria and yeast; Bennett, J. W. and LaSure, L., editors, More Gene Manipulations in Fungi, Academic Press, CA, 1991).

The cells may be cultured in any suitable container-unit, e.g. a shake flask, 24 well plates, 96 well plates, 384 well plates, 1536 well plates, or a higher number of wells per plate, or nanoliter well-less compartments.

In order to increase the number of individual activity assays performed in a given time the activity may conveniently be assayed in a high-throughput screening system using 96 well plates, 384 well plates, 1536 well plates, or a higher number of wells per plate, or nanoliter well-less compartments. Such screening techniques are well known in the art, see e.g. Dove, A., Nature Biotechnology (17), 1999, 859-863, and Kell, D., trends in Biotechnology (17), 1999, 89-91.

The molecules are recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of molecule in question.

The molecules of interest may be detected using methods known in the art that are specific for the molecules. These detection methods may include use of specific antibodies, formation of a product, or disappearance of a substrate. For example, an enzyme assay may be used to determine the activity of the molecule. Procedures for determining various kinds of activity are known in the art.

The molecules of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J-C Janson and Lars Ryden, editors, VCH Publishers, New York, 1989).

Selecting Recombinant Host Cells.

Bacillus transformations are incubated and those exhibiting desired level of reporter gene activity are selected.

As an example the reporter gene may be 2-fold over expressed in a secretion stressed cell compared to a non secretion stressed cell, preferably 5-fold over expressed in a secretion stressed cell compared to a non secretion stressed cell, more preferably 10-fold over expressed in a secretion stressed cell compared to a non secretion stressed cell, or 20-fold over expressed in a secretion stressed cell compared to a non secretion stressed cell, most preferably 50-fold over expressed in a secretion stressed cell compared to a non secretion stressed cell, or more than 100-fold over expressed in a secretion stressed cell compared to a non secretion stressed cell.

EXAMPLES

Example 1

Secretion Stress Based Screening of Transformants

Bacterial Strains and Growth Conditions

The *Bacillus subtilis* strain DN3 (Noone et al. 2000: Noone D, Howell A, and Kevin M. Devine (2000) Expression of ykdA, Encoding a *Bacillus subtilis* Homologue of HtrA, Is Heat Shock Inducible and Negatively Autoregulated. Journal of Bacteriology 182: 1592-1599) was used in this study.

It has the genotype: trpC2P spac-ykdA $P_{ykdA}$-lacZ Ery$^r$. *B. subtilis* were routinely maintained and propagated on Luria-Bertani (LB) or supplemented with agar (1.5% wt/vol) as appropriate and grown at 37° C. with aeration. X-Gal (5-bromo-4-chloro-3-indolyl-b-D-galactopyranoside) was added to the media at a concentration of 64 µg/ml, and IPTG (isopropyl-b-D-thiogalactopyranoside) was added to a final concentration of 0.8 mM. Antibiotics were added at the following concentrations: chloramphenicol, 6 µg/ml; and erythromycin, 3 µg/ml. For expression studies transformants were grown in PS-1 media for 3 days, 30° C. and at 250 rpm, cells were spun down and the supernatant analysed for secreted recombinant protein on SDS-polyacrylamide gels.

DNA Manipulations

*B. subtilis* transformations were performed as described previously (Anagnostopolous, C., and J. Spizizen. 1961. Requirements for transformation in *Bacillus subtilis*. J. Bacteriol. 81:741-746). All routine molecular biological procedures were performed according to the protocols described by Sambrook et al. (1989).

SDS-Polyacrylamide Gel Electrophoresis

Equal volume of Laemmli buffer and supernatants from liquid cultures of transformants were mixed, and analyzed on SDS-polyacrylamide gels (12%) according to Laemmli (Laemmli, U. K. (1970) *Nature* 227, 680-685)

Screening for Reporter Gene Expression

*Bacilus* transformations were plated on Petri dishes with LB-media supplemented with agar (1.5% wt/vol) and containing the appropriate antibiotics, X-Gal and IPTG at the above described concentrations. They were incubated at 37° C. overnight. Blue colonies (reportergene activity) could be seen either immediately or after up to 24 hours at room temperature.

Expression Constructs

Expression constructs were made in either the expression vector pDG268neo (Widner B; Thomas M; Sternberg D;

Lammon D; Behr R; Sloma A (2000): Development of marker-free strains of Bacillus subtilis capable of secreting high levels of industrial enzymes. Journal of Industrial Microbiology and Biotechnology, Vol. 25 (4) pp. 204-212) or in a linear integration vector. In both ways the final gene construct is integrated on the Bacillus chromosome by homologous recombination into either the AmyE locus or the pectate lyase locus. Cloning in the plasmid pDG268neo was done according to the protocols described by Sambrook et al. (1989). The linear integration vector is a PCR fusion product made by fusion of the gene of interest between two Bacillus subtils homologous chromosomal regions along with a strong promoter and a chloramphenicol resistance marker. The fusion is made by SOE PCR (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68). The promoter consists of the amyL promoter P4199 and the amyQ promoter scBAN/cry3A long stabilizer (the method is described in patent application WO03/00301). The construct NP000719 was constructed in the linear integration vector: First 3 fragments were PCR amplified: the gene fragment with specific primers oth48 (SEQ ID NO.:4) and oth50 (SEQ ID NO.:5) on genomic DNA from the strain harboring the gene (strain NN01856). The upstream flanking fragment was amplified with the primers 260558 (SEQ ID NO.: 6) and oth49 (SEQ ID NO.: 7) and the downstream flanking fragment was amplified with the primers 260559 (SEQ ID NO.: 8) and oth51 (SEQ ID NO.: 9) from genomic DNA from the strain iMB1361 (described in patent application WO 03/00301). The 3 resulting fragments were mixed in equal molar ratios (fragment 1: 400 ng, fragment 2: 100 ng, fragment 3: 200 ng) and a new PCR reaction were run under the following conditions: initial 2 min at 94° C., followed by 10 cycles of (94° C. for 15 sec., 55° C. for 45 sec., 68° C. for 5 min.), 5 cycles of (94° C. for 15 sec., 55° C. for 45 sec., 68° C. for 8 min.), 15 cycles of (94° C. for 15 sec., 55° C. for 45 sec., 68° C. for 8 min. in addition 20 sec. extra pr cycle). Two micro L of the PCR product was transformed into the Bacillus WT strain and into DN3 and selection was performed as described. The other constructs listed in table 1 are made in an identical way; the only difference is using other gene specific primers.

Strain Construction

Strain DN3 was constructed by cloning a ykdA fragment (synthesized with primers YKDA6 (SEQ ID NO.: 10) and YKDAP1 (SEQ ID NO.: 11) into pMUTin4 (Vagner V, Dervyn E and SD Ehrlich (1998) A vector for systematic gene inactivation in Bacillus subtilis. Microbiology, Vol 144, 3097-3104) to generate plasmid pDN3. Plasmid pDN3 was then integrated into the ykdA gene on the chromosome of B. subtilis strain 168 by a single crossover (Campbell-type event) to yield strain DN3. This integration results in (1) that lacZ becomes transcriptionally fused to the ykdA promoter, allowing its expression to be monitored (2) the native ykdA gene gets under the IPTG inducible Pspac promoter control, so the transcription of ykdA can be controlled by IPTG.

Results

DN3 was used as host for transformation of 12 different expression constructs. The constructs had previously been analysed in a WT bacillus host, without the possibility for secretion selection. For 5 of the constructs it was previously possible to find transformants secreting recombinant protein (from 200 mg to 2 g/L) in the WT host. For 5 of the constructs secreted recombinant protein could not be detected among selected transformants in the WT host. Two of the constructs were never previously analysed for recombinant protein, as transformants containing a non mutated gene was never obtained. In table 1 the number of white and blue colonies from each transformation is scored from the experiment using DN3 as host. Results from the experiment using the WT host are listed as well. The number of blue and white colonies reflects the result obtained with the WT host transformants: The constructs giving rise to a majority of blue colonies, were also successfully expressed in the WT (giving a band on SDS gel and containing no mutations). The constructs g iving rise to a majority of white colonies, were unsuccessfully expressed in the WT host.

Five constructs giving rise to protein bands on SDS gels (from 200 mg to 2 g/l) gave 90-99% blue colonies upon transformation of constructs into the host DN3. Five constructs for which it was not possible to find transformants in the WT host producing recombinant protein bands, gave 90-99% white colonies upon transformation into the DN3 host. Controls were transformed with water instead of DNA and this resulted in only white colonies.

Colonies from several of the constructs have been analyzed further. For 3 of the five constructs that were successfully expressed in the WT (giving recombinant protein band on SDS gel) and giving 95-99% blue colonies in DN3, blue and white colonies were analyzed further. Blue and white colonies were selected for growth in liquid culture and the culture supernatants were analyzed for recombinant proteins on SDS gels. All 3 constructs where shown to produce recombinant protein of expected size from the blue colonies, but no recombinant protein bands were observed from the white colonies.

Six of the seven construct that were not successfully expressed in the WT and gave rise to only few blue colonies in DN3 (1-30% blue colonies) were also analyzed further. For 4 of the 6 constructs it was possible to find transformants giving recombinant protein bands on SDS gels among the few blue colonies.

TABLE 1

List of constructs that were transformed into a WT host and the DN3 host. Transformants were analysed for secreted protein in supernatants from liquid cultures by SDS gel analysis. The % of blue and white colonies was scored in the DN3 host. In the WT experiment, the number of transformants with the right insert of the total number of transformants analysed is listed.

| | Expression in WT-host | | Expression in DN3 | |
|---|---|---|---|---|
| Construct/ Enzyme | Analysis of transformants insert/ analysed | Band on SDS-gel? | % blue/ white colonies | Analysis of blue colonies band on SDS-gel |
| Carboxy-peptidase | 10/10 | no | 1/99 | No band (1 blue colony analysed) |
| Alginate lyase | | no | 5/95 | Yes 300 mg/L |
| Protease | 1/10 | no | 5/95 | Yes 500 mg/L |
| Lipolytic enzyme | | no | 1/99 | No band (3 light blue colonies analysed) |
| Endopeptidase | 9/10 | no | 10/90 | Not analysed |
| Isomalto-dextranase | 3/60 | not tested | 10/90 | Yes 500 mg/L |
| Xylosidase | 12/77 | not tested | 30/70 | Yes 50-100 mg |
| Xylanase GH11 | 9/10 | yes 1-2 g/l | 90/10 | Not analysed |
| Metalloprotease | 7/10 | yes 300 mg/l | 99/1 | Yes |
| Xylanase GH11 | 9/10 | yes 100 mg/l | 95/5 | Yes |

TABLE 1-continued

List of constructs that were transformed into a WT host and the DN3 host. Transformants were analysed for secreted protein in supernatants from liquid cultures by SDS gel analysis. The % of blue and white colonies was scored in the DN3 host. In the WT experiment, the number of transformants with the right insert of the total number of transformants analysed is listed.

| | Expression in WT-host | | Expression in DN3 | |
| --- | --- | --- | --- | --- |
| Construct/ Enzyme | Analysis of transformants insert/ analysed | Band on SDS-gel? | % blue/ white colonies | Analysis of blue colonies band on SDS-gel |
| Xylanase GH10 | 8/10 | yes 1-2 g/l | 95/5 | Not analysed |
| amylase | | yes 1 g/l | 95/5 | Yes |
| Water | | | 0/100 | |

12 different constructs, including amylases, xylanases, lipases, alginate lyase, dextranase and proteases, expressing different levels of product between 200 mg and 2 gram/liter, have been assessed. In all the cases the blue/white selection system correlates with the expression potential of the constructs (blue colonies are secreting *Bacillus* transformants, white colonies are non secreting *Bacillus* transformants).

In the traditional expression cloning without secretion selection it is very time consuming to identify the transformants expressing and secreting the protein of interest. This includes analysis of transformants for the right insert by genome analysis or plasmid analysis of normally 5-20 transformants. But in some cases in table 1 we have analysed more than 70 transformants to find few with the right insert. Liquid cultures of selected t ransformants a re fermented, for protein analysis of the supernatant on SDS-gels. This step is quite labour intensive and expensive, so often only a few clones are selected for this analysis. These are sometimes non expressing clones and in the traditional expression cloning there is no way to select the f. ex 5-10% secreting transformants from the 90 to 95%. The advantage of the secretion selection is that in these cases the 5-10% expressing and secreting transformants can easily be identified by their blue colony colour on solid media.

Example 2

Secretion Stress Based Screening of a Library in *Bacillus*

Eight different *Bacillus* expression clones were selected by secretion stress based screening of a library in *Bacillus*. The eight clones express and secrete from 100 to 1000 mg/L of unknown recombinant protein.

Library Construction:
1. Modification of Vector:
The shuttle vector for *bacillus* and *E. coli* pDG268neo (Widner B; Thomas M; Sternberg D; Lammon D; Behr R; Sloma A (2000): Development of marker-free strains of *Bacillus subtilis* capable of secreting high levels of industrial enzymes. Journal of Industrial Microbiology and Biotechnology, Vol. 25 (4) pp. 204-212) was modified to allow for cloning of partial digested Sau3A or Tsp509I genomic DNA. The vector was modified by inserting a BamHI and EcoRI site between the Sac1 and Not1sites (fragment between was deleted and a linker was inserted). In this way genomic fragments can be cloned and genes contained in these fragments can be transcribed from either the strong promoter on the vector or by their own promoter.

2. Construction of a Library in *E. coli*:
Chromosomal DNA from *Bacillus flavothermus* was isolated by QIAmp Tissue Kit (Qiagen, Hilden, Germany). The genomic DNA was partial digested by Sau3A by standard methods. DNA fragments from 3-5 kb were gelpurified and ligated into BamHI digested and dephosphorylated vector (the modified pDG268neo (=pDG268BE)). 1 micro L of the ligation was transformed by electroporation into competent *E. coli* cells (Electromax DH10B Cells, Invitrogen) according to standard protocols. The transformed cells were plated on plates containing solid LB media containing ampicillin as selection marker. The plates were incubated for 16 hours at 37° C. 10-20 transformants were analysed for insert and only libraries with inserts bigger than 1 kb in 80% or more of the clones were continued. 20,000 transformants obtained this way were pooled and plasmid DNA was prepared from the pooled cells. This was done by scraping of the 20,000 colonies of plates into a buffer and purifying plasmid DNA by using a midiprep Qiagene kit (Qiagene). This plasmid pool represents the library.

3. Transformation of Library into *Bacillus subtilis* TH1:
The obtained DNA was used to transform *Bacillus* TH1 competent cells. Transformants were plated on to plates with solid LB media containing X-Gal (5-bromo-4-chloro-3-indolyl-b-D-galactopyranoside) at a concentration of 64 micro g/mL, and IPTG (isopropyl-b-D-thiogalactopyranoside) at a final concentration of 0.8 mM. Antibiotics were added at the following concentrations: chloramphenicol, 6 micro g/mL; and erythromycin, 3 micro g/mL. The plates were incubated at 37° C. for 16 hours.

4. Selection and Analysis of Transformants Secreting Recombinant Protein:
16,000-20,000 transformants were obtained. Blue colonies that occurred after 16 hours of incubation or in the following 24 hours were selected and re-streaked on new plates to obtain pure single blue colonies. For expression studies transformants were grown in liquid PS-1 or TY media for 3 days at 30° C. and at 250 rpm. Cells were spun down and the supernatant analysed for secreted recombinant protein on SDS-polyacrylamide gels.

5. Transformation Strain TH1
TH1 is a *Bacillus subtilis* strain (amy-,spo-,apr-,npr-), that has been modified by insertion of a construct, from the strain DN3 (Noone et al. 2000, J Bacteriol 182 (6) 1592-1599) by transformation and selection for Erytromycin. The changed genotype is: ykdA::pDN3 (PykdA-lacZ Pspac-ykdA) Ermr. TH1 contains the following features: the full ykdA promoter is fused to the LacZ reporter gene. In addition the ykdA gene is placed under control of the IPTG-inducible Pspac promoter, so the ykdA gene no longer has it's naturally regulation. The strain can be used as host for expression clones and libraries and transformants expressing and secreting protein can be selected on plates containing X-gal and IPTG. TH1 can be maintained on LB agar+6 micro g/mL erythromycin.

Results.
A genomic library of *Bacillus flavothermus* (NN017530) was made in the vector pDGneo268BE. The library contains 80,000 clones in all and 80% has inserts bigger than 1 kb. A plasmid pool was made from the *E. coli* library. The plasmid pool DNA was transformed into *Bacillus* strain TH1 (TH1 allows for blue/white selection of secreting recombinant clones). 16,000-20,000 *Bacillus* transformants were obtained on agar plates containing X-gal which allows for blue/white selection of secreting bacillus transformants. 25 intense blue colonies appeared among the 16,000-20,000 colonies. These blue colonies were fermented in liquid media and the supernatants analyzed on SDS-gels. 8 of the 25 blue colonies (32%) gave an intense band on an SDS gel (se SDS-gel below). The protein bands represent 6 different MW sizes, indicating that the clones express and secrete different recombinant proteins. The intensity of the recombinant bands varies representing from about 100 to 1000 mg/L recombinant protein. Seven of the 8 positive clones were characterized both by N-terminal amino acid sequence of the secreted proteins and by sequencing of the DNA insert in each. In all five different sequences from Bacillus flavothermus were obtained. After extracting the reading frame of each gene, they were analyzed for signal peptides and for transmembrane regions and finally the translated reading frame were homology searched against SWISSPROT database. Four genes encode freely secreted proteins and one gene encodes a protein without a signalpeptide (according to SignalP analysis). None of the five proteins had membrane spanning regions. In table 2 below more details of the data base searches are listed.

TABLE 2

Results from analysis of N-terminal sequences of proteins from seven clones selected by secretion stress screening.

| Clone no | Size kD | Homology to | % identity |
|---|---|---|---|
| C | 33 | unknown secreted protein | — |
| F | 42 | extracellular sugar binding protein | 58 |
| M | 46 | identical to F | — |
| H | 35 | hypothetical lipoprotein | 60 |
| R | 42 | (low homology to sugar-binding protein and ABC transporter extracellular binding protein) | 20-24 |
| D | 34 | Probably host protein sequenced (100% identical to host protein (flagelin from bacillus subtilis) | — |
| 3 | 55 | 1-pyrroline-5-carboxylate-dehyhydrogenase | 79 |

Conclusion

By this experiment we have been able to identify and isolate eight clones expressing and secreting large amounts of recombinant protein from a total number of 16,000-20,000 transformants.

The secretion stress screening does catch proteins with a signal (according to sequence analysis). A putative extracellular sugar binding protein and a putative lipoprotein was among the secreted proteins (with identifies of 58-60%). The two other secreted proteins did not show any strong homology with known proteins (one had weak homology to sugar-binding proteins and ABC transporter extracellular binding proteins).

One protein had no signal and no transmembrane regions and high homology to an intracellular carboxylate dehydrogenase (79% identity). It was found in the supernatant in large amounts. The predicted size corresponds with what was seen on the SDS gel.

Example 3

Secretion Stress Based Screening of a Non-Cult Genomic DNA Library in Bacillus

Three clones were selected by secretion stress based screening of a non-cult library in Bacillus. The three clones express and secrete around 300 mg/L of unknown recombinant protein.

Methods

DNA extraction from soil sample.

A genomic library was made from DNA isolated directly from a soil sample. DNA was extracted from the soil sample by using a "FastDNA SPIN Kit for soil" (Bio 101 Systems) and following the manufacturers protocol. Five hundred mg soil was treated with ceramic and silica particles designed to efficiently lyse all microorganisms including eubacterial spores, gram positive bacteria, yeast, algae, nematodes, and fungi. The lysate was then treated with sodium phosphate buffer and a protein precipitation solution. Subsequently the genomic DNA was extracted and purified by the use of a geneclean procedure that purifies DNA with a proprietary silica matrix and eliminates contaminants that inhibit subsequent reactions.

Library Construction and Screening in Bacillus

The non-cult library was made as described earlier for a genomic library from a single strain. The library was transformed into Bacillus TH1 and secretion stress screened as describe for a single strain genomic library.

Results

The non-cult library was transformed into Bacillus and 24000 transformants were screened on plates containing IPTG and X-gal allowing for selection of secreting transformants (blue colonies). Seven blue colonies appeared out of 24000 colonies. The seven blue transformant were grown in liquid cultures. The supernatants from liquid cultures were analysed on SDS-gels for recombinant secreted protein bands. Three of the seven colonies had a clear recombinant secreted protein band. Two different MW sizes were represented by the clones, indicating that we had at least two different secreted proteins.

The invention claimed is:

1. A method of screening a genomic library or a library of polynucleotide variants comprising at least one gene encoding a secreted protein, the method comprising the steps of:
   (i) providing a recombinant *Bacillus* bacterial host cell comprising the genomic library or a library of polynucleotide variants and a secretion stress inducible promoter operably linked to a nucleic acid sequence encoding a reporter protein or a regulator protein;
   (ii) culturing the *Bacillus* bacterial host cell under conditions promoting expression of the genomic library or library of polynucleotide variants; and
   (iii) selecting a *Bacillus* host cell which expresses the reporter protein or regulator protein and comprises the gene encoding the secreted protein.

2. The method of claim 1, wherein the secretion stress inducible promoter is operably linked to a nucleic acid sequence encoding a regulator protein which controls the expression of a reporter gene encoding a reporter protein.

3. The method of claim 2, wherein the regulator protein is an activator or repressor of the expression of the reporter gene.

4. The method of claim 1, wherein the host cell belongs to a strain selected from the group consisting of the species *Bacillus alkalophilus*, *Bacillus agaradhaerens*, *Bacillus amyloliquefaciens*, *Bacillus brevis*, *Bacillus clausii*, *Bacillus circulans*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*.

5. The method of claim 1, wherein the secretion stress inducible promoter comprises the nucleic acids 1-999 of SEQ ID NO.:1.

6. The method of claim 1, wherein the secretion stress inducible promoter consists of the nucleic acids 1-999 of SEQ ID NO.:1.

7. The method of claim 1, wherein the secretion stress inducible promoter in its normal position is the promoter linked to a gene encoding a polypeptide which has at least 99% identity to the amino acid sequence of SEQ ID NO.:2.

8. The method of claim 1, wherein the secretion stress inducible promoter is the promoter linked to a gene encoding a polypeptide which has at least 95% identity to the amino acid sequence of SEQ ID NO.:2.

9. The method of claim 1, wherein the secretion stress inducible promoter comprises the repeated octameric motif of SEQ ID NO.: 3.

10. The method of claim 2, wherein the reporter protein is 2-fold over expressed in a secretion stressed cell compared to a non secretion stressed cell.

11. The method of claim 2, wherein the reporter protein is selected from the group consisting of fluorescent protein, antibiotic markers, and substrate converting enzymes.

12. The method of claim 1, wherein the secretion stress inducible promoter comprises nucleic acids 1-999 of SEQ ID NO.:1, and the host cell further comprises a IPTG-inducible promoter operably linked to a nucleic acid sequence encoding the amino acids 1 to 449 of SEQ ID NO:2.

13. The method of claim 1, wherein the secretion stress inducible promoter consists of nucleic acids 1-999 of SEQ ID NO.:1, and the host cell further comprises a IPTG-inducible promoter operably linked to a nucleic acid sequence encoding the amino acids 1 to 449 of SEQ ID NO:2.

14. The method of claim 1, wherein the secreted protein is an enzyme.

15. The method of claim 14, wherein the secreted protein is an enzyme selected from the group consisting of proteases, endoglucanases, beta-glucanases, hemicellulases, lipases, peroxidases, laccases, alpha-amylases, glucoamylases, cutinases, pectinases, reductases, oxidases, phenoloxidases, ligninases, pullulanases, pectate lyases, xyloglucanases, xylanases, pectin acetyl esterases, polygalacturonases, rhamnogalacturonases, pectin lyases, mannanases, pectin methylesterases, cello-biohydrolases, transglutaminases and phytases.

* * * * *

SEQUENCE LISTING

```
<160> NUMBER OF SEQ ID NOS: 11

<210> SEQ ID NO 1
<211> LENGTH: 2349
<212> TYPE: DNA
<213> ORGANISM: Bacillus subtilis
<220> FEATURE:
<221> NAME/KEY: YkdA_protein
<222> LOCATION: (1000)..(2349)
<223> OTHER INFORMATION: 1-999 is promoter
<220> FEATURE:
<221> NAME/KEY: CDS
<222> LOCATION: (1000)..(2349)

<400> SEQUENCE: 1
```

```
tctttcaagg attcatgttt gtttaccaac ctgttctgta agcagttcat attttctcag      60
ggttctttca aatacctcat caaaaacgtc cggcacagag gcgtgtatca cctcagctcc     120
ctctcccgtt attccgcctt tggttgcaac acgttccagc gtctcctcga aagacatatt     180
tttttcgatc agcatcttgc cagttccgta tagcgaatga atcagaaaat caaaggcttc     240
ttctttggac aggctgctgt ttctgacggc agacagtgcc agttcttcaa agattgcagc     300
tatgaatccc ggtgccgagc tcgttaaatt gctggccaca tctaaattcg attcttgat      360 ttcccgtaca cggctgaaaa ccgataacaa ttcattcaga cgttcttttt tctctgcagc     420
cagtgcttca ctgtgaacga caagtgagat gccggcttct gcttcggacg taatggcagg     480
aataacacgt gagataccgg cttctgtttc tgcctccaaa agacgcagcg gcacaccggc     540
agctatggat acgatgtgag tatttctgtt cacatacggg tacagacggc gcattgtttc     600
gatgacatgg agtggcggga cgcatatcaa aatcaattgg cacgtatttg cccaattctc     660
caacggatca gccgatacgt ttggataatc tgacatgagt gcccgcagcc gctccccctt     720
cgttctcgtc tcaataaata gctcattctc ttttatttgt tcatgtttca acagctgtct     780
agcgatcata tccgccatgc tgccatatcc aatcaatcca atctgttcca tcgactcagt     840
cctttcatat acaatatgaa gtgtaccgtt ttccgcactt tttcacaatt tcccataatc     900
ttttcatttt tatcccacag ttttttgttta tgataaactc aagtcataaa cctatcaata     960
taaatagaca tgtgaaaata gagaaacgga gtgaacatg atg gat aac tat cgt         1014
                                            Met Asp Asn Tyr Arg
                                              1               5 gat gaa aac aga acg aaa ggt aat gag aat gag gtc ttt tta acg aaa        1062
Asp Glu Asn Arg Thr Lys Gly Asn Glu Asn Glu Val Phe Leu Thr Lys
             10                  15                  20 gag aac gat cag agc gcc tcc tac tcg gcc cgc aat gtc att cat gat        1110
Glu Asn Asp Gln Ser Ala Ser Tyr Ser Ala Arg Asn Val Ile His Asp
         25                  30                  35 cag gag aag aaa aaa cga gga ttc gga tgg ttc aga ccg ttg ctt ggc        1158
Gln Glu Lys Lys Lys Arg Gly Phe Gly Trp Phe Arg Pro Leu Leu Gly
     40                  45                  50 gga gtg atc ggc ggc agt ctt gct ctt ggc att tac acg ttt aca ccg        1206
Gly Val Ile Gly Gly Ser Leu Ala Leu Gly Ile Tyr Thr Phe Thr Pro
 55                  60                  65 ctt ggt aac cat gat tct cag gac act gca aaa caa tca tcc agc cag        1254
Leu Gly Asn His Asp Ser Gln Asp Thr Ala Lys Gln Ser Ser Ser Gln
 70                  75                  80                  85 cag caa acg caa tct gtt aca gca aca agc acc tcc tct gaa tct aaa        1302
Gln Gln Thr Gln Ser Val Thr Ala Thr Ser Thr Ser Ser Glu Ser Lys
             90                  95                 100 aaa agc tca agc agc tca tct gca ttc aag agc gag gac tct tct aaa        1350
Lys Ser Ser Ser Ser Ser Ala Phe Lys Ser Glu Asp Ser Ser Lys
            105                 110                 115 atc tca gat atg gta gaa gac ctt tca cca gcg att gtc ggt att aca        1398
Ile Ser Asp Met Val Glu Asp Leu Ser Pro Ala Ile Val Gly Ile Thr
        120                 125                 130 aat ctt cag gca caa tca aac agc tct ttg ttc ggc tct agt tct tct        1446
Asn Leu Gln Ala Gln Ser Asn Ser Ser Leu Phe Gly Ser Ser Ser Ser
        135                 140                 145 gat tcc agc gaa gat aca gaa agc ggt tca ggg tca ggt gtc att ttc        1494
Asp Ser Ser Glu Asp Thr Glu Ser Gly Ser Gly Ser Gly Val Ile Phe
150                 155                 160                 165 aaa aaa gag aat ggc aag gct tat atc att aca aat aac cac gtc gta        1542
Lys Lys Glu Asn Gly Lys Ala Tyr Ile Ile Thr Asn Asn His Val Val
                170                 175                 180
```

```
gaa ggg gca tca tca ctg aag gta tct tta tat gac ggc act gag gtt      1590
Glu Gly Ala Ser Ser Leu Lys Val Ser Leu Tyr Asp Gly Thr Glu Val
            185                 190                 195 act gca aag ctg gta ggc agt gac tcg tta act gat tta gcc gtc ctc      1638
Thr Ala Lys Leu Val Gly Ser Asp Ser Leu Thr Asp Leu Ala Val Leu
        200                 205                 210 caa atc agt gat gac cac gtc aca aaa gtg gca aac ttc ggt gat tca      1686
Gln Ile Ser Asp Asp His Val Thr Lys Val Ala Asn Phe Gly Asp Ser
    215                 220                 225 tct gat ctt aga aca ggc gag acc gtt att gcg att ggg gat ccg ctt      1734
Ser Asp Leu Arg Thr Gly Glu Thr Val Ile Ala Ile Gly Asp Pro Leu
230                 235                 240                 245 gga aaa gac ctg tcc cgc aca gta aca caa gga att gta agc ggc gtg      1782
Gly Lys Asp Leu Ser Arg Thr Val Thr Gln Gly Ile Val Ser Gly Val
                250                 255                 260 gac aga acg gtt tca atg tct aca tca gcc ggc gaa acg agc att aac      1830
Asp Arg Thr Val Ser Met Ser Thr Ser Ala Gly Glu Thr Ser Ile Asn
            265                 270                 275 gtc att cag aca gac gca gca att aat cca ggt aac agc ggc ggt cct      1878
Val Ile Gln Thr Asp Ala Ala Ile Asn Pro Gly Asn Ser Gly Gly Pro
        280                 285                 290 ttg tta aat aca gac ggc aaa att gtc ggc att aac agt atg aaa atc      1926
Leu Leu Asn Thr Asp Gly Lys Ile Val Gly Ile Asn Ser Met Lys Ile
    295                 300                 305 agt gag gat gat gtt gag ggt atc gga ttc gcc att cca agc aat gac      1974
Ser Glu Asp Asp Val Glu Gly Ile Gly Phe Ala Ile Pro Ser Asn Asp
310                 315                 320                 325 gta aaa ccg att gct gaa gaa ttg ctg tct aaa gga caa att gaa cgt      2022
Val Lys Pro Ile Ala Glu Glu Leu Leu Ser Lys Gly Gln Ile Glu Arg
                330                 335                 340 cca tat atc ggt gtc agc atg ctt gat cta gag caa gtg ccg caa aat      2070
Pro Tyr Ile Gly Val Ser Met Leu Asp Leu Glu Gln Val Pro Gln Asn
            345                 350                 355 tac caa gaa ggc aca ctc ggc ctg ttc ggc agc cag ctg aat aaa ggc      2118
Tyr Gln Glu Gly Thr Leu Gly Leu Phe Gly Ser Gln Leu Asn Lys Gly
        360                 365                 370 gtt tac atc cgt gag gtc gct tca ggc tct cct gct gaa aag gcc gga      2166
Val Tyr Ile Arg Glu Val Ala Ser Gly Ser Pro Ala Glu Lys Ala Gly
    375                 380                 385 tta aaa gcg gag gat att atc atc ggc cta aaa ggt aaa gaa att gat      2214
Leu Lys Ala Glu Asp Ile Ile Ile Gly Leu Lys Gly Lys Glu Ile Asp
390                 395                 400                 405 aca ggc agt gaa ttg cgc aat atc tta tat aaa gac gca aag atc ggt      2262
Thr Gly Ser Glu Leu Arg Asn Ile Leu Tyr Lys Asp Ala Lys Ile Gly
                410                 415                 420 gat acc gtt gaa gtg aaa att ctc cga aac ggc aaa gaa atg acg aaa      2310
Asp Thr Val Glu Val Lys Ile Leu Arg Asn Gly Lys Glu Met Thr Lys
            425                 430                 435 aaa att aaa ctg gat caa aaa gaa gag aaa act tcg taa                  2349
Lys Ile Lys Leu Asp Gln Lys Glu Glu Lys Thr Ser
        440                 445
```

<210> SEQ ID NO 2
<211> LENGTH: 449
<212> TYPE: PRT
<213> ORGANISM: Bacillus subtilis

<400> SEQUENCE: 2

```
Met Asp Asn Tyr Arg Asp Glu Asn Arg Thr Lys Gly Asn Glu Asn Glu
1               5                   10                  15
```

```
Val Phe Leu Thr Lys Glu Asn Asp Gln Ser Ala Ser Tyr Ser Ala Arg
            20                  25                  30

Asn Val Ile His Asp Gln Glu Lys Lys Arg Gly Phe Gly Trp Phe
            35                  40                  45

Arg Pro Leu Leu Gly Gly Val Ile Gly Gly Ser Leu Ala Leu Gly Ile
50                      55                  60

Tyr Thr Phe Thr Pro Leu Gly Asn His Asp Ser Gln Asp Thr Ala Lys
65                      70                  75                  80

Gln Ser Ser Ser Gln Gln Gln Thr Gln Ser Val Thr Ala Thr Ser Thr
                    85                  90                  95

Ser Ser Glu Ser Lys Lys Ser Ser Ser Ser Ser Ala Phe Lys Ser
                100                 105                 110

Glu Asp Ser Ser Lys Ile Ser Asp Met Val Glu Asp Leu Ser Pro Ala
                115                 120                 125

Ile Val Gly Ile Thr Asn Leu Gln Ala Gln Ser Asn Ser Ser Leu Phe
            130                 135                 140

Gly Ser Ser Ser Ser Asp Ser Ser Glu Asp Thr Glu Ser Gly Ser Gly
145                     150                 155                 160

Ser Gly Val Ile Phe Lys Lys Glu Asn Gly Lys Ala Tyr Ile Ile Thr
                    165                 170                 175

Asn Asn His Val Val Glu Gly Ala Ser Ser Leu Lys Val Ser Leu Tyr
            180                 185                 190

Asp Gly Thr Glu Val Thr Ala Lys Leu Val Gly Ser Asp Ser Leu Thr
            195                 200                 205

Asp Leu Ala Val Leu Gln Ile Ser Asp His Val Thr Lys Val Ala
            210                 215                 220

Asn Phe Gly Asp Ser Ser Asp Leu Arg Thr Gly Glu Thr Val Ile Ala
225                 230                 235                 240

Ile Gly Asp Pro Leu Gly Lys Asp Leu Ser Arg Thr Val Thr Gln Gly
                245                 250                 255

Ile Val Ser Gly Val Asp Arg Thr Val Ser Met Ser Thr Ser Ala Gly
                260                 265                 270

Glu Thr Ser Ile Asn Val Ile Gln Thr Asp Ala Ala Ile Asn Pro Gly
            275                 280                 285

Asn Ser Gly Gly Pro Leu Leu Asn Thr Asp Gly Lys Ile Val Gly Ile
290                 295                 300

Asn Ser Met Lys Ile Ser Glu Asp Asp Val Glu Gly Ile Gly Phe Ala
305                 310                 315                 320

Ile Pro Ser Asn Asp Val Lys Pro Ile Ala Glu Glu Leu Leu Ser Lys
                325                 330                 335

Gly Gln Ile Glu Arg Pro Tyr Ile Gly Val Ser Met Leu Asp Leu Glu
            340                 345                 350

Gln Val Pro Gln Asn Tyr Gln Glu Gly Thr Leu Gly Leu Phe Gly Ser
            355                 360                 365

Gln Leu Asn Lys Gly Val Tyr Ile Arg Glu Val Ala Ser Gly Ser Pro
            370                 375                 380

Ala Glu Lys Ala Gly Leu Lys Ala Glu Asp Ile Ile Gly Leu Lys
385                 390                 395                 400

Gly Lys Glu Ile Asp Thr Gly Ser Glu Leu Arg Asn Ile Leu Tyr Lys
                405                 410                 415

Asp Ala Lys Ile Gly Asp Thr Val Glu Val Lys Ile Leu Arg Asn Gly
                420                 425                 430
```

```
Lys Glu Met Thr Lys Lys Ile Lys Leu Asp Gln Lys Glu Glu Lys Thr
            435                 440                 445
Ser

<210> SEQ ID NO 3
<211> LENGTH: 8
<212> TYPE: DNA
<213> ORGANISM: Artificial
<220> FEATURE:
<223> OTHER INFORMATION: octameric motif
<220> FEATURE:
<221> NAME/KEY: octameric_motif
<222> LOCATION: (1)..(8)

<400> SEQUENCE: 3 ttttcata                                                             8

<210> SEQ ID NO 4
<211> LENGTH: 44
<212> TYPE: DNA
<213> ORGANISM: Artificial
<220> FEATURE:
<223> OTHER INFORMATION: Primer
<220> FEATURE:
<221> NAME/KEY: Primer_oth48
<222> LOCATION: (1)..(44)

<400> SEQUENCE: 4
gttcatcgat cgcatcggct aatcagacca cttcgggtga aggc                    44

<210> SEQ ID NO 5
<211> LENGTH: 50
<212> TYPE: DNA
<213> ORGANISM: Artificial
<220> FEATURE:
<223> OTHER INFORMATION: Primer
<220> FEATURE:
<221> NAME/KEY: Primer_oth50
<222> LOCATION: (1)..(50)

<400> SEQUENCE: 5
ggagcggatt gaacatgcga ttaaatatcc ttcgagacat tttcgatcgc              50

<210> SEQ ID NO 6
<211> LENGTH: 21
<212> TYPE: DNA
<213> ORGANISM: Artificial
<220> FEATURE:
<223> OTHER INFORMATION: Primer
<220> FEATURE:
<221> NAME/KEY: Primer_260558
<222> LOCATION: (1)..(21)

<400> SEQUENCE: 6
gagtatcgcc agtaagggc g                                              21

<210> SEQ ID NO 7
<211> LENGTH: 44
<212> TYPE: DNA
<213> ORGANISM: Artificial
<220> FEATURE:
<223> OTHER INFORMATION: Primer

<400> SEQUENCE: 7
gccttcaccc gaagtggtct gattagccga tgcgatcgat gaac                    44

<210> SEQ ID NO 8
```

```
<211> LENGTH: 23
<212> TYPE: DNA
<213> ORGANISM: Artificial
<220> FEATURE:
<223> OTHER INFORMATION: Primer
<220> FEATURE:
<221> NAME/KEY: Primer_260559
<222> LOCATION: (1)..(23)

<400> SEQUENCE: 8
gcagccctaa aatcgcataa agc                                                23

<210> SEQ ID NO 9
<211> LENGTH: 50
<212> TYPE: DNA
<213> ORGANISM: Artificial
<220> FEATURE:
<223> OTHER INFORMATION: Primer
<220> FEATURE:
<221> NAME/KEY: Primer_oth51
<222> LOCATION: (1)..(50)

<400> SEQUENCE: 9
gcgatcgaaa atgtctcgaa ggatatttaa tcgcatgttc aatccgctcc                   50

<210> SEQ ID NO 10
<211> LENGTH: 28
<212> TYPE: DNA
<213> ORGANISM: Artificial
<220> FEATURE:
<223> OTHER INFORMATION: Primer
<220> FEATURE:
<221> NAME/KEY: Primer_YKDA6
<222> LOCATION: (1)..(28)

<400> SEQUENCE: 10
gcgaattcta aactcaagtc ataaacct                                           28

<210> SEQ ID NO 11
<211> LENGTH: 26
<212> TYPE: DNA
<213> ORGANISM: Artificial
<220> FEATURE:
<223> OTHER INFORMATION: Primer
<220> FEATURE:
<221> NAME/KEY: Primer_YKDAP1
<222> LOCATION: (1)..(26)

<400> SEQUENCE: 11
gcggatccga tgatgaatga cattgc                                             26
```